United States Patent
Pegram et al.

(10) Patent No.: US 7,918,125 B2
(45) Date of Patent: Apr. 5, 2011

(54) METHODS AND DEVICES TO TEST DIFFUSION RATES OF OCULAR DRUG DELIVERY SYSTEMS

(75) Inventors: Stephen C. Pegram, Jacksonville, FL (US); Shivkumar Mahadevan, Orange Park, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 177 days.

(21) Appl. No.: 11/930,597

(22) Filed: Oct. 31, 2007

(65) Prior Publication Data
US 2008/0190221 A1 Aug. 14, 2008

Related U.S. Application Data

(60) Provisional application No. 60/863,587, filed on Oct. 31, 2006.

(51) Int. Cl.
*G01N 15/08* (2006.01)
(52) U.S. Cl. .......................................... 73/38; 73/64.47
(58) Field of Classification Search ............... 73/36, 38, 73/64.47
See application file for complete search history.

(56) References Cited

U.S. PATENT DOCUMENTS

| | | | |
|---|---|---|---|
| 5,627,071 A * | 5/1997 | Triva | 435/307.1 |
| 5,710,302 A | 1/1998 | Kunzler | |
| 5,760,100 A | 6/1998 | Nicolson | |
| 5,776,999 A | 7/1998 | Nicolson | |
| 5,789,461 A | 8/1998 | Nicolson | |
| 5,817,924 A * | 10/1998 | Tuomela et al. | 73/38 |
| 5,849,811 A | 12/1998 | Nicolson | |
| 5,965,631 A | 10/1999 | Nicolson | |
| 5,998,498 A | 12/1999 | Vanderlaan | |
| 6,087,415 A | 7/2000 | Vanderlaan | |
| 6,298,713 B1 * | 10/2001 | Nandu et al. | 73/64.47 |
| 6,395,756 B2 * | 5/2002 | Trimming et al. | 514/324 |
| 6,951,894 B1 * | 10/2005 | Nicolson et al. | 523/107 |
| 7,332,128 B2 | 2/2008 | Fernando | |
| 2001/0006968 A1 * | 7/2001 | Trimming et al. | 514/254.07 |
| 2003/0024829 A1 | 2/2003 | Matsuzawa et al. | 206/5.1 |
| 2003/0103201 A1 * | 6/2003 | Frumusa et al. | 356/124 |
| 2004/0241207 A1 | 12/2004 | Chauhan | |
| 2005/0260249 A1 * | 11/2005 | Neely et al. | 424/427 |
| 2006/0177483 A1 * | 8/2006 | Byrne et al. | 424/427 |
| 2008/0100795 A1 * | 5/2008 | Dubey et al. | 351/159 |
| 2008/0233006 A1 * | 9/2008 | Kennedy et al. | 422/68.1 |

FOREIGN PATENT DOCUMENTS

| | | |
|---|---|---|
| EP | 406161 | 1/1991 |
| JP | 06074893 A * | 3/1994 |
| JP | 944074893 A | 3/1994 |
| JP | 2000016905 | 1/2000 |
| JP | 2005104970 A * | 4/2005 |
| WO | WO 94/21698 | 9/1994 |
| WO | WO 03053480 A1 * | 7/2003 |
| WO | WO 2006/084275 | 8/2006 |

OTHER PUBLICATIONS

Morrison et al., "Permeability of Hydrophilic Contact Lenses", Investigative Opthamology, Jan. 1972.*

(Continued)

*Primary Examiner* — David A. Rogers

(57) ABSTRACT

Methods of detecting the discharge and uptake rates of ophthalmic lenses containing pharmaceutical agents are disclosed herein.

14 Claims, 3 Drawing Sheets

OTHER PUBLICATIONS

Uchida et al., "Azulene Incoporation and Release by Hydrogel Containing Methacrylamide Propyltrimenthylammonium Chloride, and its Application to Soft Contact Lenses", Journal of Controlled Release, vol. 92, 2003.*

Karlgard, C. et al., "In vitro uptake and release studies of ocular pharmaceutical agents by silicon-containing and p-HEMA hydrogel contact lens materials", International Journal of Pharmaceutics, Amsterdam, Netherlands, vol. 257, No. 1-2, May 2003, pp. 141-151.

Alvarez-Loreno et al., "Imprinted soft contact lenses as norfloxacin delivery system", Journal of Controlled Release, Amsterdam, Netherlands, vol. 113, No. 3, Jul. 2006, pp. 236-244.

Hirantani, H. et al., "The nature of backbone monomers determines the performance of imprinted soft contact lenses as timolol drug delivery systems", Biomaterials, Elsevier Science Publishers BV, Barking, Great Brittian, vol. 25, No. 6, Mar. 2004, pp. 1105-1113.

PCT Search Report Application No. PCT/US2007/082335, mailed Jun. 13, 2008.

* cited by examiner

METHODS AND DEVICES TO TEST DIFFUSION RATES OF OCULAR DRUG DELIVERY SYSTEMS

RELATED APPLICATION

This application is a non-provisional filing of a provisional application, U.S. Ser. No. 60/863,587, filed on Oct. 31, 2006.

FIELD OF THE INVENTION

This invention related to devices and methods to test the diffusion rates of pharmaceutical agents through ophthalmic lens.

BACKGROUND

Most diseases of the eye are treated with topical ophthalmic solutions containing pharmaceutical agents. It has been postulated that delivery and efficacy of these agents would be greatly increased if the agents were incorporated in ophthalmic lenses and those lenses were used as drug delivery devices. These agents may be added to the ophthalmic lenses by a variety of methods including soaking the agent into a formed lens, adding the agent to the formulation of the lens prior to its formation and the like. Despite the teachings of many, to date, there are no commercially available products for patients.

In order to gain approval for such a device, one must demonstrate the rate at which the pharmaceutical agent diffuses into and out of the ophthalmic lens. One of the possible reasons for the lack of commercial products is that current test methods to demonstrate dissolution rates of pharmaceutical agents through contact lenses are cumbersome. These methods rely on discrete sampling and are known to be labor intensive and expensive. In addition, these methods do not allow one to obtain continuous dissolution data. Therefore, it would be useful if devices and methods that to determine dissolution rates, and more particularly, continuous dissolution rates of pharmaceutical agents through ophthalmic lenses, would be useful. This need is met by the following invention

DETAILED DESCRIPTION OF THE INVENTION

Figure 1:
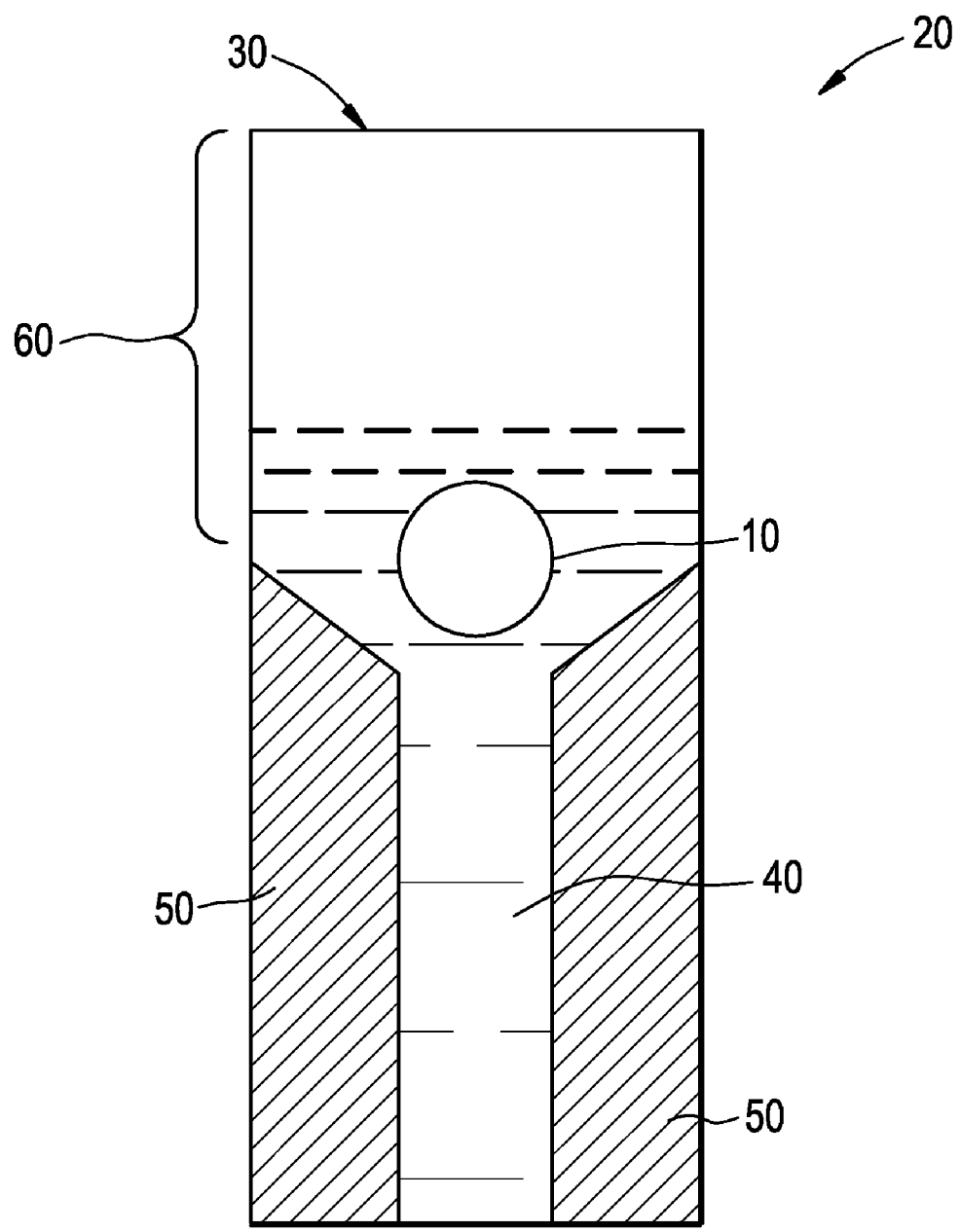
FIG. 1 Illustrates a container with a sample area and a detecting area
FIG. 2. Illustrates a decoupled testing apparatus
FIG. 3. Illustrates a closed testing apparatus.

This invention includes a method of measuring the discharge rate of a pharmaceutical agent from an ophthalmic lens, wherein the method comprises the steps of (a) placing said ophthalmic lens comprising said pharmaceutical agent in a container comprising a sample chamber and a detecting chamber, wherein said sample chamber is sized to contain an ophthalmic lens and an effective amount of a solution and said detecting chamber is sized contain a second amount the solution, but is not sized to contain an ophthalmic lens, wherein said sample chamber and said detecting chamber are connected to allow solution to flow between said sample chamber to said detecting chamber but to contain said ophthalmic lens within said sample chamber, (b) monitoring the detecting chamber to determine the presence or absence of said pharmaceutical agent in solution contained within said detecting chamber.

As used herein, "pharmaceutical agents refers to pharmaceutical or nutraceutical compounds used to treat conditions of the eye, and such compound degrade in the presence of oxygen and certain transition metals. Examples of pharmaceutical compounds include antihistamines, antibiotics, antibacterial agents, antiviral agents, antifungal agents, analgesics, anesthetics, antiallergenic agents, mast cell stabilizers, steroidal and non-steroidal anti-inflammatory agents, angiogenesis inhibitors; antimetabolites, fibrinolytics, neuroprotective drugs, angiostatic steroids, mydriatics, cyclopegic mydriatics; miotics; vasoconstrictors; vasodilators, anticlotting agents; anticancer agents, antisense agents, immunomodulatory agents, carbonic anhydrase inhibitors, integrin antabonistsl; cyclooxygenase inhibitors, VEGF antagonists; immunosuppressant agents and the like. Particularly, examples of pharmaceutical compounds include but are not limited to acrivastine, antazoline, astemizole, azatadine, azelastine, buclizine, bupivacaine, cetirizine, clemastine, cyclizine, cyproheptadine, ebastine, emedastine, ephedrine, eucatropine, fexofenadine, homatropine, hydroxyzine, ketotifen, levocabastine, levoceterizine, lomefloxacin, meclizine, mepivacaine, mequitazine, methdilazine, methapyrilene, mianserin, naphazoline norastemizole, norebastine, ofloxacin, oxymetazoline, pheniramine, phenylephrine, physostigmine, picumast, promethazine, scopolamine, terfenadine, tetrahydozoline, thiethylperazine, timolol, trimeprazine, triprolidine, pharmaceutically acceptable salts and mixtures thereof. Preferred pharmaceutical compounds include acrivatine, antazoline, astemizole, azatadine, azelastine, clemastine, cyproheptadine, ebastine, emedastine, eucatropine, fexofenadine, homatropine, hydroxyzine, ketotife, levocabastine, levoceterizine, meclizine, mequitazine, methdialazine, methapyrilene, norastemizole, norebastine, oxymetazoline, physootigmine, picumast, promethazine, scopolamine, terfenadine, tetrahyerozoline, fimilol, trimeprazine, triprolidine, and pharmaceutically acceptable salts thereof. Particularly preferred pharmaceutical compounds include phenarimine, ketotifen, ketotifen fumarate nor ketotifen fumarate, 11-dihydro-11-(1-methyl-4-piperidinylidene)-5H-imidazo[2,1-b][3] benzazepine-3-carboxaldehyde (CAS# 147084-10-4), olapatadine and mixtures thereof. More particularly preferred pharmaceutical compounds include ketotifen fumarate, 11-dihydro-11-(1-methyl-4-piperidinylidene)-5H-imidazo[2,1-b][3] benzazepine-3-carboxaldehyde (CAS# 147084-10-4) and mixtures thereof.

Examples of nutraceutical compounds include vitamins and supplements such as vitamins A, D, E, lutein, zeaxanthin, lipoic acid, flavonoids, ophthalmicially compatible fatty acids, such as omega 3 and omega 6 fatty acids, combinations thereof, combinations with pharmaceutical compounds and the like. The methods of the invention may be used to detect the discharge rate (or uptake rate) of ophthalmic lenses containing about 8 μg or more of pharmaceutical agent. Preferably, the discharge rate for ophthalmic lenses that contain about 8 μg to about 90 μg, more preferably about 10 μg to about 40 μg, more preferably about 10 μg to about 25 μg may be determined by the methods of this invention.

As used herein, "ophthalmic lens" refers to a device that resides in or on the eye. These devices can provide optical correction or may be cosmetic. Ophthalmic lenses include but are not limited to soft contact lenses, intraocular lenses, overlay lenses, ocular inserts, and optical inserts. The preferred lenses of the invention are soft contact lenses made from silicone elastomers or hydrogels, which include but are not limited to silicone hydrogels, and fluorohydrogels. Soft contact lens formulations are disclosed in U.S. Pat. No. 5,710,302, WO 9421698, EP 406161, JP 2000016905, U.S. Pat. Nos. 5,998,498, 6,087,415, 5,760,100, 5,776,999, 5,789,461, 5,849,811, and 5,965,631. The foregoing references are hereby incorporated by reference in their entirety. The particularly preferred ophthalmic lenses of the inventions are known by the United States Approved Names of acofilcon A, alofilcon A, alphafilcon A, amifilcon A, astifilcon A, atalafilcon A, balafilcon A, bisfilcon A, bufilcon A, comfilcon, crofilcon A, cyclofilcon A, darfilcon A, deltafilcon A, deltafilcon B, dimefilcon A, drooxifilcon A, epsifilcon A, esterifilcon A, etafilcon A, focofilcon A, galfilcon A, genfilcon A, govafilcon A, hefilcon A, hefilcon B, hefilcon D, hilafilcon A, hilafilcon B, hioxifilcon B, hioxifilcon C, hixoifilcon A, hydrofilcon A, lenefilcon A, licryfilcon A, licryfilcon B, lidofilcon A, lidofilcon B, lotrafilcon A, lotrafilcon B, mafilcon A, mesifilcon A, methafilcon B, mipafilcon A, nelfilcon A, netrafilcon A, ocufilcon A, ocufilcon B, ocufilcon C, ocufilcon D, ocufilcon E, ofilcon A, omafilcon A, oxyfilcon A, pentafilcon A, perfilcon A, pevafilcon A, phemfilcon A, polymacon, senofilcon A, silafilcon A, siloxyfilcon A, tefilcon A, tetrafilcon A, trifilcon A, vifilcon, and xylofilcon A. More particularly preferred ophthalmic lenses of the invention are galfilcon A, genfilcon A, lenefilcon A, senofilcon A, comfilcon, lotrafilcon A, lotrafilcon B, and balafilcon A. The most preferred lenses include etafilcon A, nelfilcon A, hilafilcon, vifilcon, and polymacon.

"Detecting chamber" refers to an enclosure that houses the solution but not the ophthalmic lens. It is attached to the sampling chamber to permit solution to flow from one chamber to the other. The detecting chamber may be closed, open, or connected to other devices such as an HPLC. The detecting chamber preferably contains an optically transparent portion. This optically transparent portion permits light to pass through to the ophthalmic lens and the solution as well as reflect light from those sources. It is preferred that the detecting chamber contain an optically transparent portion.

As used herein "sample chamber" refers to an enclosure that is attached to the detecting chamber to permit the flow of solution from one chamber to the other. The sample chamber may be closed open, or connected to a device that delivers solutions, other ophthalmic lenses, inert gases and the like to the chamber.

The "solutions" that are used in methods of this invention may be water-based solutions. Typical solutions include, without limitation, saline solutions, other buffered solutions, and deionized water. The preferred aqueous solution is deoinized water or saline solution containing salts including, without limitation, sodium chloride, sodium borate, sodium phosphate, sodium hydrogenphosphate, sodium dihydrogenphosphate, or the corresponding potassium salts of the same. These ingredients are generally combined to form buffered solutions that include an acid and its conjugate base, so that addition of acids and bases cause only a relatively small change in pH. The buffered solutions may additionally include 2-(N-morpholino)ethanesulfonic acid (MES), sodium hydroxide, 2,2-bis(hydroxymethyl)-2,2',2"-nitrilotriethanol, n-tris(hydroxymethyl)methyl-2-aminoethanesulfonic acid, citric acid, sodium citrate, sodium carbonate, sodium bicarbonate, acetic acid, sodium acetate, ethylenediamine tetraacetic acid and the like and combinations thereof. Preferably, the solution is a borate buffered or phosphate buffered saline solution or deionized water. The particularly preferred solution contains about 1,850 ppm to about 18,500 ppm sodium borate, most particularly preferred about 3,700 ppm of sodium borate. The "effective amount" of the solution is enough to immerse the lens, but not so much that the level of pharmaceutical agent that is discharged from the lens (or as described below absorbed by the lens) cannot be detected. The preferred effective amount is about 1 mL to about 3 mL, more preferably about 1 mL to about 2 mL. The "second amount" of solution is substantially similar to the effective amount but is not necessarily equivalent to the effective amount. It is preferred that the second amount is about 0.5 mL to about 3 mL, more prefereably about 0.5 mL to about 1 mL.

As used herein "monitoring" refers to methods of analyzing the solution to determine the concentration of pharmaceutical agent in the solution. Examples of such detecting methods include but are not limited to HPLC, UV Spectormeters and the like. The preferred monitoring method is UV visible spectroscopy.

Further the invention includes, a method of measuring the uptake rate of a pharmaceutical agent to an ophthalmic lens, wherein the method comprises the steps of (a) placing said ophthalmic lens in container comprising a sample chamber and a detecting chamber, wherein said sample chamber is sized to contain an ophthalmic lens and an effective amount of a solution and said detecting chamber is sized to contain a second amount the solution, but is not sized to contain an ophthalmic lens, wherein said sample chamber and said detecting chamber are connected to allow solution to flow between said sample chamber to said detecting chamber but to contain said ophthalmic lens within said sample chamber and said effective amount of solution and said second amount of solution comprise a pharmaceutical agent, (b) monitoring the detecting chamber to determine the presence or absence of said pharmaceutical agent in solution contained within said detecting chamber. The terms pharmaceutical agent, sample chamber, ophthalmic lens detecting, chamber, solution, effective amount, second amount and monitoring all have their aforementioned meanings and preferred ranges.

FIG. 1 illustrates a chamber that is used in the methods of the invention. An ophthalmic lens 10 and a solution are inserted into container 20 from end 30. The solution fills the detecting chamber 40 and the sample chamber 60. Detecting chamber 40 is bordered on its sides by solid areas 50. Lens 10 rests in the sample chamber 60, which starts at end 30 and terminates in at the detecting area. Container 20 is made of an optically transparent material area. A UV-Vis spectrometer is placed above the detecting chamber and the spectrometer monitors the amount of increase or decrease at wavelengths associated with the pharmaceutical agent.

Still further the invention includes, a method of measuring the discharge rate of a pharmaceutical agent from an ophthalmic lens, wherein the method comprises the steps of (a) placing said ophthalmic lens comprising said pharmaceutical agent a testing apparatus, wherein said testing apparatus is sized to enclose said ophthalmic lens and to permit solutions to contact said ophthalmic lens, (b) placing said enclosed ophthalmic lens into a sufficient amount of solutions, (c) monitoring sufficient amount of solution to determine the presence or absence of said pharmaceutical agent in said solution.

The terms pharmaceutical agent, ophthalmic lens, solution(s) and monitoring all have their aforementioned meanings and preferred ranges. The term "sufficient amount" refers to the quantity of solution that permits one to monitor the pharmaceutical agent as it disperses from the ophthalmic lens. For example, if an ophthalmic lens contains about 100 mg of ketotifen fumarate, and the solution is deionized water, the sufficient amount of deionized water is about 25 mL.

Figure 2:
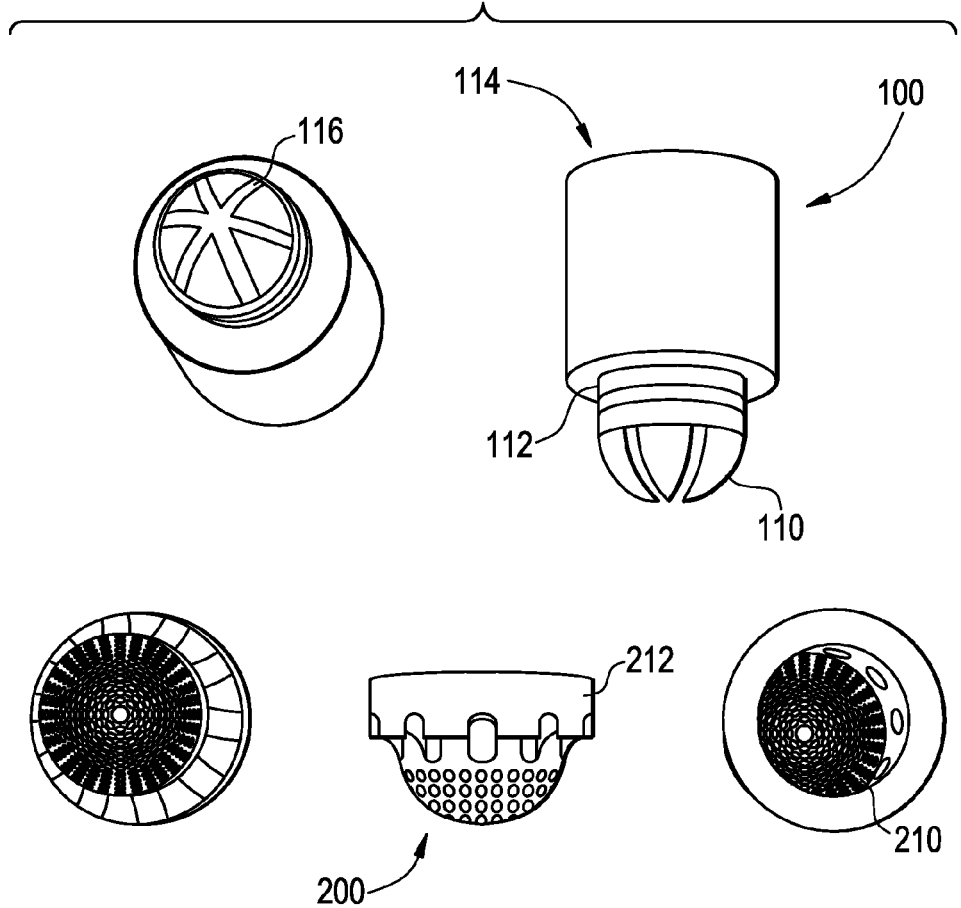
Figure 3:
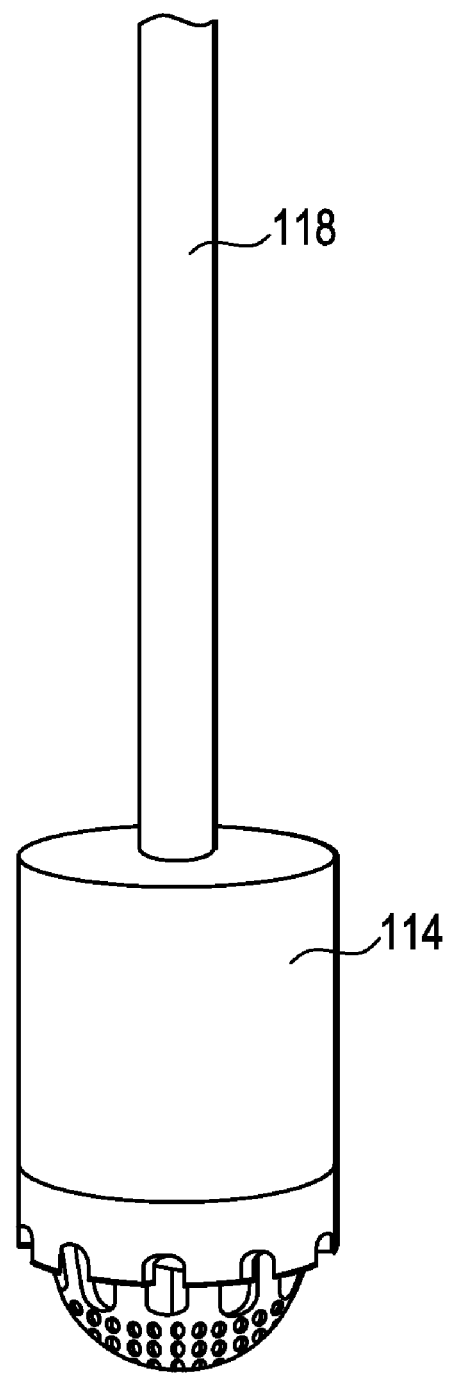

The term testing apparatus refers to a container that encloses the ophthalmic lens and permits solution to flow through said lens. FIGS. 2 and 3, illustrate a suitable testing apparatus.

Male top 100 contains a convex portion 110, an O-ring 112 and holder 114. The convex portion 110 has several radial openings 116, to permit solution to reach an ophthalmic lens enclosed in the testing apparatus. The female bottom 200 has a concave portion 210 and a seating ridge 212 that is sized to mate with the male top when the testing apparatus is closed. The concave portion 210 contains several apertures to permit solution to reach enclosed ophthalmic lenses. Even though the concave and convex portions of the testing device are illustrated with apertures and radial openings, either piece can contains such openings, or any other suitable openings. FIG. 3 illustrates that holder 114 is adapted to connect to a shaft 118. This shaft is connected to a motor that rotates the testing apparatus in solutions. In the preferred methods of the invention, the testing apparatuses are rotated during diffusion testing.

In order to illustrate the invention the following examples are included. These examples do not limit the invention. They are meant only to suggest a method of practicing the invention. Those knowledgeable in contact lenses as well as other specialties may find other methods of practicing the invention. However, those methods are deemed to be within the scope of this invention.

EXAMPLES

Example 1

Preparation of Ophthalmic Lenses Containing 25 µg of Ketotifen Fumarate

To prepare 1000 g of a 25 µg/mL ketotifen fumarate ("K-25:
1. 9.10 g of boric acid
2. 1.00 g of sodium borate decahydrate
3. 8.30 g of sodium chloride
4. 0.10 g of Ca2DTPA
5. 981.475 g of deionized water
6. 0.025 g of ketotifen fumarate The system is maintained at room temperature throughout the solution making process. All components 1-6 are added in any order and stirred using a magnetic or mechanical stirrer until the solution is homogeneous. Ketotifen fumarate is added last and the mixture is stirred for an additional 30 minutes or as long as it takes to make the solution homogeneous.

1-Day Acuvue® Brand Contact Lenses (etafilcon A +3.00) were removed from their packages and repackaged in glass vials containing 3.0 mL of the 25 µg/mL ketotifen fumarate solutions described above to produce K-Lens 25. The vials were sealed with PTFE coated rubber stoppers and heated for 18 minutes at 124° C.

Example 2

Discharge of Ketotifen

A lens of Example 1 was placed in a chamber of FIG. 1 with 1 mL of packaging solution (ingredients 1-5 of Example 1 in the same proportions) that does not contain ketotifen. UV-VIS spectrometer readings were taken at 299 nm at one minute intervals and plotted to determine the dissolution rate of ketotifen from the lens.

Example 3

Uptake of Ketotifen

A 1-Day Acuvue® Brand Contact Lens was placed in a chamber of FIG. 1 with 1 mL of the 25 µg/mL ketotifen fumarate of Example 1. UV-VIS spectrometer readings were taken at 299 nm at one minute intervals and plotted to determine the uptake rate of ketotifen to the lens.

What is claimed is
1. A method of measuring the discharge rate of a pharmaceutical agent from an ophthalmic lens, wherein the method comprises the steps of
   (a) immersing said ophthalmic lens comprising said pharmaceutical agent into the sample chamber of a container comprising a sample chamber and a detecting chamber, wherein said sample chamber is sized to contain an ophthalmic lens and an effective amount of a solution and said detecting chamber is sized contain a second amount the solution, but is not sized to contain an ophthalmic lens, wherein said sample chamber and said detecting chamber are connected to allow solution to flow between said sample chamber to said detecting chamber but to contain said ophthalmic lens within said sample chamber,
   (b) monitoring the detecting chamber to determine the presence or absence of said pharmaceutical agent in solution contained within said detecting chamber.

2. The method of claim 1 wherein the pharmaceutical agent is selected from the group consisting of acrivastine, antazoline, astemizole, azatadine, azelastine, buclizine, cetirizine, clemastine, cromolyn, cyclizine, cyproheptadine, ebastine, emedastine, epinastine, fexofenadine, hydroxyzine, ketorolac tromethamine, ketotifen, levocabastine, levoceterizine, lodoxamide, loteprednol, mepivacaine, mequitazine, methdilazine, methapyrilene, norastemizole, norebastine, olopatadine, picumast, promethazine, terfenadine, trimeprazine, triprolidine, and pharmaceutically acceptable salts and mixtures thereof.

3. The method of claim 1 wherein the pharmaceutical agent is selected from the group consisting of acrivatine, antazoline, astemizole, azatadine, azelastine, clemastine, cyproheptadine, ebastine, emedastine, fexofenadine, hydroxyzine, ketotifen, levocabastine, levoceterizine, mequitazine, methdialazine, methapyrilene, norastemizole, norebastine, picumast, promethazine, terfenadine, trimeprazine, triprolidine, and pharmaceutically acceptable salts and mixtures thereof.

4. The method of claim 1 wherein the pharmaceutical agent is selected from the group consisting of ketotifen, ketotifen, nor ketotifen, 11-dihydro-11-(1-methyl-4-piperidinylidene)-5H-imidazo[2,1-b][3]benzazepine-3-carboxaldehyde, olapatadine, and pharmaceutically acceptable salts and mixtures thereof.

5. The method of claim 1 wherein the ophthalmic lens is selected from the group consisting of acofilcon A, acofilcon A, alofilcon A, alphafilcon A, amifilcon A, astifilcon A, atalafilcon A, balafilcon A, bisfilcon A, bufilcon A, comfilcon, crofilcon A, cyclofilcon A, darfilcon A, deltafilcon A, deltafilcon B, dimefilcon A, drooxifilcon A, epsifilcon A, esterifilcon A, etafilcon A, focofilcon A, galfilcon A, genfilcon A, govafilcon A, hefilcon A, hefilcon B, hefilcon D, hilafilcon A, hilafilcon B, hioxifilcon B, hioxifilcon C, hioxifilcon A, hydrofilcon A, lenefilcon A, licryfilcon A, licryfilcon B, lidofilcon A, lidofilcon B, lotrafilcon A, lotrafilcon B, mafilcon A, mesifilcon A, methafilcon B, mipafilcon A, nelfilcon A, netrafilcon A, ocufilcon A, ocufilcon B, ocufilcon C, ocufilcon D, ocufilcon E, ofilcon A, omafilcon A, oxyfilcon A, pentafilcon A, perfilcon A, pevafilcon A, phemfilcon A, polymacon, senofilcon A, silafilcon A, siloxyfilcon A, tefilcon A, tetrafilcon A, trifilcon A, vifilcon, and xylofilcon A.

6. The method of claim 1 wherein the ophthalmic lens is selected from the group consisting of galfilcon A, genfilcon A, lenefilcon A, senofilcon A, comfilcon, lotrafilcon A, lotraifilcon B, and balafilcon A.

7. The method of claim 1 wherein the ophthalmic lens is selected from the group consisting of etafilcon A, nelfilcon A, hilafilcon, vifilcon, and polymacon.

8. The method of claim 1 wherein the ophthalmic lens is etafilcon A and the pharmaceutical agent is selected from the group consisting of ketotifen, ketotifen, nor ketotifen, 11-dihydro-11-(1-methyl-4-piperidinylidene)-5H-imidazo[2,1-b][3]benzazepine-3-carboxaldehyde, olapatadine, and pharmaceutically acceptable salts and mixtures thereof.

9. The method of claim 1 wherein the ophthalmic lens is etafilcon A and the pharmaceutical agent is ketotifen or pharmaceutically acceptable salts and mixtures thereof.

10. The method of claim 1 wherein the ophthalmic lens is etafilcon A the pharmaceutical agent is ketotifen or pharmaceutically acceptable salts and mixtures thereof, and the amount of ketotifen or pharmaceutically acceptable salts and mixtures thereof contained with said ophthalmic lens is about 8 μg to about 90 μg.

11. The method of claim 1 wherein the ophthalmic lens is etafilcon A the pharmaceutical agent is ketotifen or pharmaceutically acceptable salts and mixtures thereof, and the amount of ketotifen or pharmaceutically acceptable salts and mixtures thereof contained with said ophthalmic lens about 10 μg to about 40 μg.

12. The method of claim 1 wherein the ophthalmic lens is etafilcon A the pharmaceutical agent is ketotifen or pharmaceutically acceptable salts and mixtures thereof, and amount of ketotifen or pharmaceutically acceptable salts and mixtures thereof contained with said ophthalmic lens is about 10 μg to about 25 μg.

13. The method of claim1 wherein the effective amount is about 1 mL to about 3 mL.

14. The method of claim 1 wherein the second amount is about 0.5 mL to about 3 mL.

* * * * *